Figure 1:
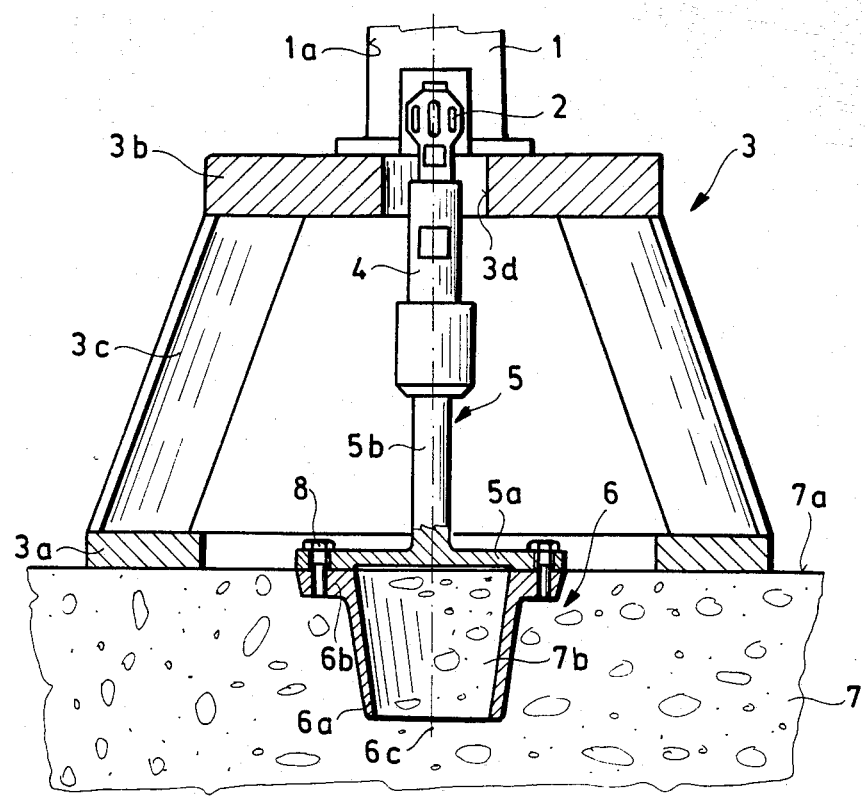

United States Patent [19]

Mehes et al.

[11] Patent Number: 4,501,153

[45] Date of Patent: Feb. 26, 1985

[54] TEST MACHINE FOR DETERMINING CONCRETE STRENGTH

[76] Inventors: Ferenc Mehes, Báthori u. 24., Budapest, Hungary, 1054; András Mózes, Karpat u. 54., Budapest, Hungary, 1133

[21] Appl. No.: 440,211

[22] PCT Filed: Feb. 23, 1982

[86] PCT No.: PCT/HU82/00006

§ 371 Date: Oct. 4, 1982

§ 102(e) Date: Oct. 4, 1982

[87] PCT Pub. No.: WO82/02949

PCT Pub. Date: Sep. 2, 1982

[30] Foreign Application Priority Data

Feb. 23, 1981 [HU] Hungary ................................ 432/81

[51] Int. Cl.³ ........................ G01N 3/08; G01N 33/38
[52] U.S. Cl. ..................................................... 73/803
[58] Field of Search ............... 73/803, 864.51, 827, 73/834, 845; 264/31

[56] References Cited

U.S. PATENT DOCUMENTS

| | | | |
|---|---|---|---|
| 3,176,053 | 3/1965 | Stasio | 264/31 |
| 3,541,845 | 11/1970 | Kierkegaard-Hansen | 73/803 |
| 3,595,072 | 7/1971 | Richards | 73/803 |
| 3,861,201 | 1/1975 | Kaindl | 73/803 |
| 4,103,540 | 8/1978 | McLaughlin | 73/803 X |

*Primary Examiner*—Charles A. Ruehl
*Attorney, Agent, or Firm*—Young & Thompson

[57] ABSTRACT

A test machine for determining the strength of concrete which is suitable to perform quality tests of structures or structural elements within the plant or at the site. The machine has a loading unit provided with a force measuring means. A breaking cup is embedded in the concrete to be tested when it is wet, an extractor head being fixed to the breaking cup, serving for extraction thereof from the solidified concrete, and between the force measuring means and the extractor head there is inserted a joint ending in a releasable connecting piece.

9 Claims, 6 Drawing Figures

TEST MACHINE FOR DETERMINING CONCRETE STRENGTH

The invention relates to a test machine for determining concrete strength, especially for performing quality tests of concrete structures or structural elements within the plant or at the site. The machine is provided with a loading unit loading the concrete until destruction. The loading unit applies tension on some part of the concrete and it is provided with a device for determining the crumbling strength causing destruction e.g. with a force measuring means. The force measuring means is set on a support arranged on the surface of the concrete to be tested.

In the field of concrete and reinforced concrete building, when either applying prefabricated structures or erecting monolithic buildings, there is needed the possibility to determine technical parameters of the solidified concrete, first of all the mechanical properties thereof. From the earliest days of building with concrete it has been customary to prepare particular test pieces, so-called test-cubes or more rarely test pieces of special form, which are loaded until destruction and from the crumbling strength a conclusion can be drawn in respect of the concrete strength.

These tests provide, however, only informatory results and full safety conclusions can not be drawn therefrom as to the mechanical properties of the completed structure. The first and most important reason for this resides in that, as a matter of course, the pouring circumstances of the test pieces differ from those of the concrete of the actual structure. Besides, solidifying of the raw concrete may also take place under substantially different conditions.

Experience has shown that the strength parameters measured on test pieces give an unrealistically good result. Thus, efforts have been made for a number of years to perform also mechanical tests based on fracturing samples taken from the actual structures and on evaluation of the results of these fractures.

In the course of this latter procedure, samples e.g. test cubes are cut out from the finished structure at predetermined locations, then these are loaded until fracture. Such a method can, however, in many cases not be used firstly on account of the damage to the structure and secondly because there can be some special reasons due to which the whole of the structure must not be broken down nor the load thereon shifted by the stress accompanying the cutting work. This was the motive leading to a solution wherein punches of different forms are embedded in the concrete material before it solidifies and from the force needed to extract them, a conclusion may be drawn as to the mechanical properties.

The experiences with this test method were not unambiguously advantageous since during extraction of the punch, the fractured cross section will be accidental i.e. it will have a different form and size in each case. Thus, in spite of carefully measuring the force, the measured value is not reliable enough due to the inaccurately known cross section. One of such measuring methods is described in U.S. Pat. No. 4,103,540.

More reliable tests than the above-mentioned "punch extraction" are those wherein from the values of the pore space and of the water-cement coefficient a conclusion is drawn to the concrete strength. One of these methods is described in the GDR Pat. No. 102,043. On more or less similar considerations are based also those accelerated methods for determining strength described in patents Nos. CD Pat. No. 2,607,919, U.S. Pat. No. 3,974,679 and Fr Pat. No. 2,323,149. All these solutions have the common deficiency that due to uncertain basic data, the conclusions to be drawn from the test will be vague.

A further advance in concrete testing was achieved by procedures in which the sample is cast in the concrete element to be tested. Such methods are to be found in the patents Nos., DE Pat. Nos. 1,917,242, 1,917,730 and U.S. 3,176,053. According to these methods so-called trial cores are cast in and then removed from the concrete to be tested and thereafter they are loaded until fracture on a testing machine.

As most expedient is found the variation of the latter method according to which telescopic double sleeves are embedded in the concrete element. Also with these more developed procedures the uncertainty of the fractured cross section is more or less prevalent and this results in the test results being hardly to be compared to each other.

In the field in question, the most modern testing methods are considered to be those using samples cut out from the solidified concrete element and, from measuring the ultimate tensile load a conclusion is drawn to the mechanical properties. Typical examples of such methods are described in U.S. Pat. No. 3,861,201 and in the essentially identical Austrian Pat. No. 320,313. This method is suitable for determining strength properties of concretes and in general subsequently solidified materials, wherein solids of special shapes are embedded in the material and then extracted after solidifying of the material.

This method contains several good ideas. However, it has the drawback that the test result does not represent directly the ultimate tensile strength but a fictitious crumbling strength which is influenced also by a number of different parameters such as compression strength, bending-tensile strength and even the shearing strength of the concrete. Thus, it is very difficult to compare the qualities of different concretes.

On a more or less similar consideration is based also the test method serving to determine strength characteristics of materials manufactured by casting and subsequent solidifying described in the U.S. Pat. No. 3,541,845. The reliability of this method is less than that of the former because the extracted test pieces are loaded simultaneously by shearing stress and by tensile stress. The stresses may, due to different local circumstances, develop and in given case be dominant with a high degree of accidentality.

There have been similar experiments with apparatus serving solely for testing concrete and reinforced structures as described in U.S. Pat. No. 3,595,072. Its main drawback consists in that one can not state a simple and strict correlation between the test results and the actual so-called cube strength of the concrete.

The same is true of the disclosure in French Pat. No. 2,313,677. By this latter method only the bending strength is to be stated and also in this case the local faults of casting and of other circumstances causing a wide variation of the test results and casting doubt on the comparability thereof, play an important role.

The invention aims at developing a test machine on the one hand suitable to perform quality tests both in plants and at the site and on the other hand retaining the advantages of the method according to which the test piece is extracted from the concrete element by simultaneously eliminating the deficiences originating, in the case of the known solutions, from the uncertain cross section of the fracture.

Within said field, the invention provides a solution giving direct information about the strength of the built-in structure, enabling tests to be performed at low costs in a quick and simple manner, and performing tests with a minimum variance, with a high degree of test safety and reliability.

The inventive idea is based on the recognition that direct information relating to the built-in concrete element or structure and simultaneously a test result in unique correlation to the cube strength, can be achieved when the test machine by its construction ensures that under the effect of the tensile load, the fracture will result always at the same place, along a determined cross section. Thereby not only can the high degree of variance accompanying the known test machines be eliminated but at the same time a simple device for quality control is achieved which can be operated without special qualification.

In accordance with these objects, a test machine is to determine the strength of concrete, especially to perform quality tests of concrete structures or structural elements within the plant or at the site, comprising a loading unit for loading the concrete until destruction, the loading unit applying tensile stress on some part of the concrete. The machine is provided with a device for determining the crumbling strength causing destruction e.g. with a force measuring means, and the force measuring means is set on a support arranged on the surface of the concrete to be tested. In the concrete to be tested, when it is wet, a breaking cup is embedded, an extractor head being fixed to the breaking cup serving for extraction thereof from the already solidified concrete and fixed to the breaking cup by a force transmitting connection. A joint ending in a preferably threaded connecting piece is inserted between the force measuring means and the extractor head.

Figure 2:
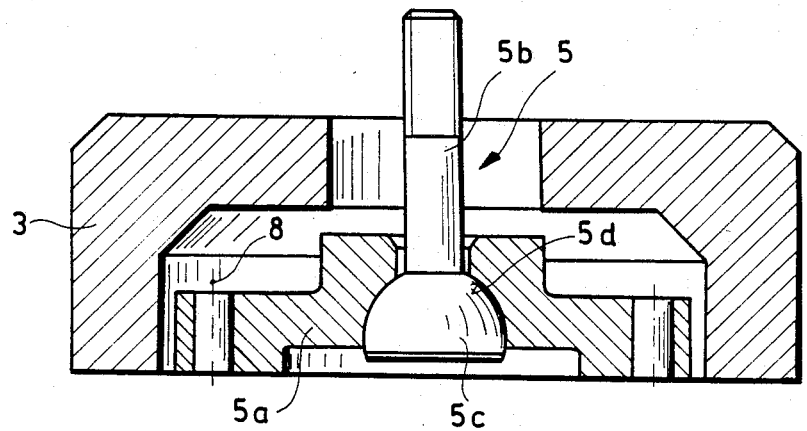
Figure 3:
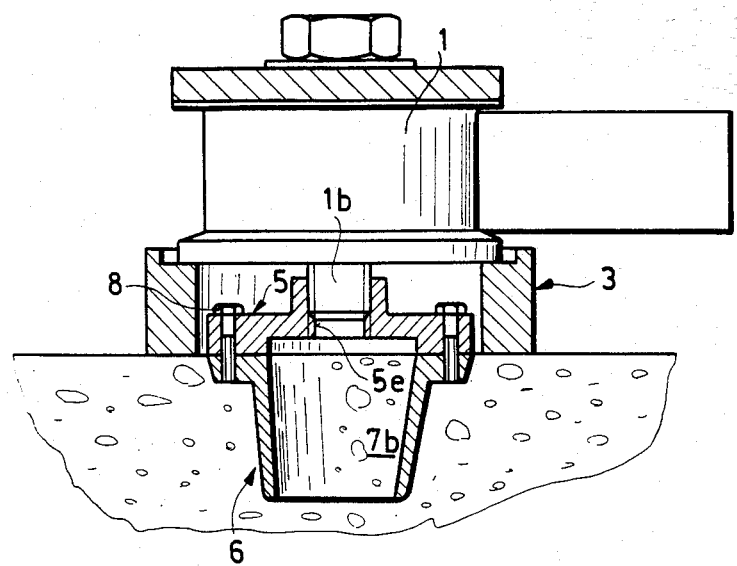
Figure 4:
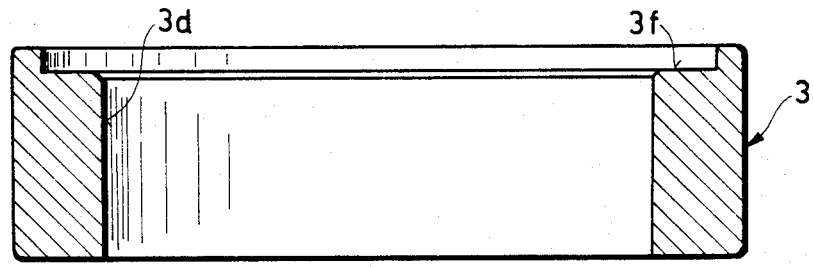
Figure 5:
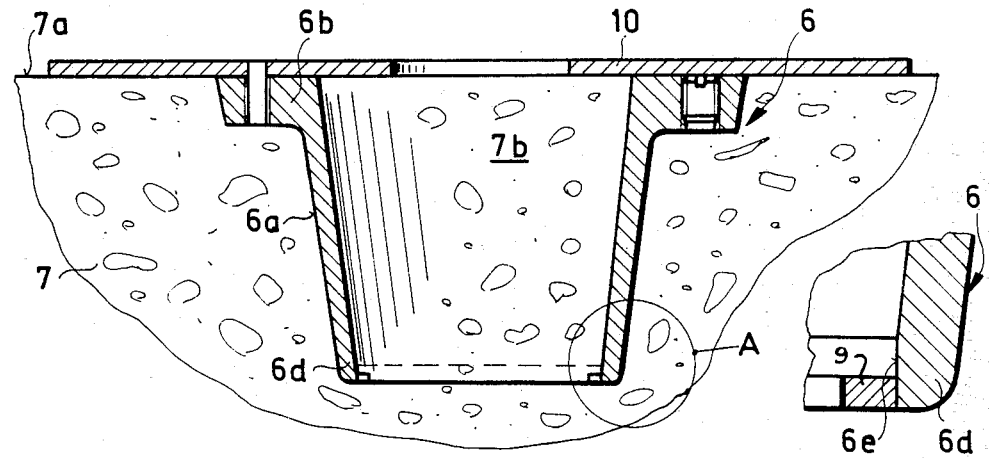
Figure 6:

The invention will be described below in greater detail on the basis of the accompanying drawings: In the drawings FIG. 1 is a schematic longitudinal section through a possible embodiment of the test machine, FIG. 2 shows the longitudinal section of another embodiment, FIG. 3 is the longitudinal section of a third embodiment, FIG. 4 shows a possible embodiment of the supporting device used instead of the supporting frame, FIG. 5 shows the breaking cup, and FIG. 6 shows an enlarged fragment of FIG. 5.

In FIG. 1 there is shown in schematic longitudinal section, a breaking cup 6 embedded within the concrete 7, having a frusto-conical mantle 6a with a cross section reducing in size from the surface 7a of the concrete 7 inwardly of the concrete 7. To the mantle 6a there is connected a collar 6b made preferably as a unit therewith, being fixed rigidly yet in a releasable manner to an extractor head 5 by screws 8 which are preferably parallel to the longitudinal axis 6c of the breaking cup 6.

The extractor head 5 consists, according to FIG. 1, of a disc 5a and a shaft 5b preferably formed as one piece. Along the periphery of the disc 5a and of the collar 6b there are provided bores to coincide with each other, in which the screws 8 can be set. Between the extractor head 5 and the force measuring means known per se and being not the subject matter of the present invention, there is inserted a joint 4 ending in a connecting piece 2 and serving for transmitting the load from the force measuring means 1 to the extractor head 5.

The joint 4 may be connected to the extractor head 5 in a releasable manner e.g. via threaded connection or bayonet locking. The connecting piece 2 can preferably be turned in relation to the joint 4, and the force measuring means 1 is provided with a housing 1a to receive the connecting piece 2.

To support the force measuring means 1 and to stabilize its position in relation to the structure of the concrete 7, a supporting frame 3 is provided. In the case of the embodiment shown in FIG. 1 the supporting frame 3 consists of a base ring 3a set on the surface 7a of the concrete 7, of a supporting disc 3b to set the force measuring means 1 thereon, and of legs 3c connecting 3a and 3b with each other.

Instead of legs 3c there can be provided a single "skirt" having a mantle of e.g. truncated pyramid or truncated cone form. In either case there is of course a need to provide in the supporting disc 3b a central hole 3d to let the joint 4 pass through.

In FIG. 2 there is shown an extractor head 5 in longitudinal section, wherein the disc 5a is provided with a liner 5d in the form of a concave socket. The liner 5d forms with the ball 5a a ball-and-socket joint, and enables a small relative turning between the disc 5a and the shaft 5b.

Due to the special construction, the concrete cake 7b inside the breaking cup 6 is extracted always by tensile load only. Thus, the breaking cup 6 is never subject to an eccentric load causing sticking and thereby disturbing the test result.

In FIG. 3 an embodiment is shown wherein the extracting force is transmitted from the force measuring means 1 to the extractor head 5 via a screw-thread. In this case, the extractor head 5 is provided with a threaded bore 5e engaging a threaded bolt 1b forming part of the force measuring means 1.

In FIG. 4 the most simple form of the supporting frame 3 is shown as a supporting ring, having a central hole 3d. Preferably, the supporting ring is provided with a shoulder 3f suitable to set the force measuring means 1 thereon.

In the course of the test, the breaking cup 6 with the downwardly narrowing cross section is arranged in the concrete structure or concrete element to be tested, at a predetermined place, when the raw concrete is not yet solidified. It is advisable now to snap some kind of a cap 10 (as shown in FIG. 5a) upon the collar 6b, in order to prevent the raw concrete from penetrating into the bores of the collar 6b.

The cap further serves to facilitate setting the upper face of the collar 6b of the breaking cup 6 parallel to the surface 7a of the concrete 7. It may also be of advantage to lubricate the outer side of the mantle 6a of the breaking cup 6 with some anti-adhesion material e.g. with grease or separating oil in order to prevent the concrete from bonding there, as otherwise this would eventually influence the test result.

After the concrete has solidified, at a predetermined time the cap 10 will be taken off the breaking cup 6, then by fitting the extractor head 5 thereto and by inserting and fastening the screws 8 a force transmitting connection is provided through joint 4 and connecting piece 2 with the force measuring means 1. By operating the force measuring means 1, the extraction force is slowly and progressively increased until the concrete cake 7b is torn off from the surface of the concrete 7.

In FIG. 6 it can be seen that the end flange 6d of the breaking cup 6 on its side facing the concrete cake 7b, ends in a cylindrical mantle 6e the generatrix of which is parallel to the longitudinal axis of the breaking cup 6. By this construction it is ensured that the concrete cake 7b shall be torn off along the flange 6d. In certain cases the breaking circumstances may further be improved when in the cylinder mantle 6e a flexible ring 9 made of e.g. plastics or metal is inserted.

Experiments show that the quotient of the force value read off at the moment of breaking, against the fractured cross section, gives a strength value which is unambiguously characteristic of the concrete as tested. This is due first of all to the fact that the concrete cake 7b formed as a truncated cone will be torn off always along a cylindrical mantle having a generatrix parallel to the direction of the tensile force and perpendicular to the longitudinal axis.

The measuring accuracy of the test machine according to the invention fulfils even the highest production requirements. It is suitable to replace the conventional cube breaking procedure. It offers the possibility to perform measuring at several points on the structure, enabling thereby better quality control and, through the safety test, makes it possible to realize structures while saving cement. The breaking cups 6 may remain in the concrete 7 since they are preferably made of stainless steel. Thus, during the lifetime of the structure measuring can be performed also at a later date and thereby it is possible to determine ageing properties of the concrete.

What we claim is:

1. A test machine for determining the strength of concrete, comprising a loading unit for loading the concrete until destruction by applying tensile stress to a portion of the concrete, a support for supporting the loading unit against a surface of the concrete to be tested, a breaking cup adapted to be embedded in wet concrete which when hardened is to be tested, said breaking cup being hollow and having an open inner end which is the end embedded deepest in the concrete, the side walls of said cup converging toward said open inner end, and means connecting said loading unit with said cup to draw said cup out of the concrete after the concrete is set, thereby to fracture the concrete along a plane extending across said open inner end of the breaking cup.

2. A test machine as claimed in claim 1, in which said side walls of the breaking cup are a figure of rotation of an imaginary line about an axis parallel to the direction in which the breaking cup is drawn out of the concrete.

3. A test machine as claimed in claim 2, in which said figure of rotation is a truncated cone.

4. A test machine as claimed in claim 3, in which said inner end is circular.

5. A test machine as claimed in claim 1, in which said breaking cup has an outwardly extending flange about its outer end opposite said inner end, for attaching the breaking cup to the loading unit.

6. A test machine as claimed in claim 5, in which said means connecting the breaking cup to the loading unit comprises an extractor head to which said flange is releasably connected by screws.

7. A test machine as claimed in claim 1, in which said open inner end of the breaking cup has an inner surface which is a shallow cylinder.

8. A test machine as claimed in claim 7, and a flexible ring disposed in said shallow cylinder.

9. A test machine as claimed in claim 1, said means connecting said breaking cup to said loading unit including a ball and socket joint on the breaking cup.

* * * * *